United States Patent [19]

Larose et al.

[11] Patent Number: 5,868,998
[45] Date of Patent: Feb. 9, 1999

[54] METHOD FOR THE MICROAEROSOL FUMIGATION OF NEWLY HATCHED POULTRY

[75] Inventors: Rene N. Larose; Joseph A. Schultz, both of Glastonbury, Conn.

[73] Assignee: Arbor Acres Farm, Inc., Glastonbury, Conn.

[21] Appl. No.: 952,684

[22] Filed: Sep. 29, 1992

Related U.S. Application Data

[63] Continuation of Ser. No. 721,296, Jun. 26, 1991, abandoned.
[51] Int. Cl.$^6$ ....................................................... A61L 2/00
[52] U.S. Cl. .................................. 422/28; 422/32; 422/36
[58] Field of Search ................................... 422/36, 32, 28; 119/6.8, 3, 159, 160

[56] References Cited

U.S. PATENT DOCUMENTS

| | | | |
|---|---|---|---|
| 2,751,882 | 6/1956 | Coyner | 119/159 |
| 2,984,240 | 5/1961 | Eames | 119/160 |
| 2,993,832 | 7/1961 | Kaitz | 119/160 |
| 3,148,649 | 9/1964 | Moore et al. | 119/159 |
| 3,936,270 | 2/1976 | Gunther | 422/33 |
| 4,674,490 | 6/1987 | Frankel et al. | 119/160 |
| 4,717,544 | 1/1988 | Calcaterra et al. | 422/36 |
| 4,850,997 | 7/1989 | DuBose | 119/160 |
| 4,912,357 | 3/1990 | Drews et al. | 239/102.2 |
| 4,930,200 | 6/1990 | Mckown | 239/102.2 |
| 4,932,359 | 6/1990 | Sheldon et al. | 119/6.8 |

*Primary Examiner*—Laura Edwards
*Attorney, Agent, or Firm*—Robert S. Smith

[57] ABSTRACT

A method of fumigation which will destroy microorganisms in the environment of hatching and newly hatched poultry whereby a disinfecting solution such as hydrogen peroxide is applied into the environment by a microaerosol. The method significantly reduces the level of microorganisms in the environment and reduces the risk of post hatch transfer of potentially disease causing microorganisms, without adversely affecting the viability of the newly hatched poultry.

19 Claims, No Drawings

METHOD FOR THE MICROAEROSOL FUMIGATION OF NEWLY HATCHED POULTRY

This is a continuation of application Ser. No. 07/721,296, filed Jun. 26, 1991 now abandoned.

BACKGROUND OF THE INVENTION

The present invention relates to a method for reducing microorganisms in the environment of newly hatched poultry which reduces the chance of transmission of disease in the hatchery.

The environment of newly hatched poultry quickly becomes contaminated with microorganisms as soon as the actual hatching process or exit from the eggs begins. The microorganisms include, but are not limited to, (1) bacteria such as Salmonella species, *Escherichia coli, staphylococcus aureus* and (2) fungal organisms such as members of fungal genus Aspergillus, and possibly avian Mycoplasmas. This rapid rise in the concentration of microorganisms is often referred to as a bacterial bloom which follows the pipping stage of incubation in poultry. It is at his stage that optimum conditions for growth of microorganisms exists in terms of humidity, temperature, and nutrient levels. Organic debris present from the hatching process provides abundant levels of nutrients enhancing microbial replication at this time.

The microbial levels in this environment are commonly measured by microbiological culture of air or by measurement of microbial levels contained on specific quantities of hatcher down or fluff (a by product of the bird produced during hatch).

The method required by government regulation for at least the last 40 years to reduce this environmental contamination is to generate formaldehyde gas by either physically mixing formalin with potassium permanganate, or more conveniently by evaporating formalin on a continuous basis during the last few days of the hatching process. While the use of formaldehyde does reduce the level of microorganisms in the environment it is becoming more difficult to use due to the public health concerns about exposure of humans to this compound.

Another significant concern with the use of formaldehyde in the post pipping stage of hatching is the adverse effect of this compound of the physical integrity of the avian respiratory system. Published literature documents this affect. The physical damage caused to the avian respiratory system by formaldehyde may predispose the animals to increased susceptibility to respiratory disease encountered in the early days of life.

It will be understood that while the invention has application to the environment of avian chicks after they are hatched and that the method in accordance will affect the portion of chicks that survive. Thus, one effect of the use of the method in accordance is to improve the hatchability of eggs since that term is defined as the portion of chicks that survive the hatching process.

The incubation process in commercially raised-avian species such as chickens and turkeys is conventionally carried out initially in setters and then in a type of incubator referred to as a hatcher. In the hatcher the respiratory system of the embryo converts to a direct air breathing animal (the pipping stage), as opposed to air exchange across the egg shell. The control of temperature and humidity are especially critical at this point of hatching. Levels of moisture too high or too low will interfere with the hatching process and result in decreased hatch percentage and or inferior post hatch performance of hatched poultry.

It is because of this that a gaseous disinfectant such as formaldehyde is desirable because it can be administered continuously from the point of pipping when the microorganism bloom occurs up until essentially all the poultry have exited from the egg without significantly increasing the moisture level in the environment. The time for this to happen may be up to thirty hours which precludes conventional methods of disinfectant application such as spraying, conventional automatic foggers or even continuous administration through the hatcher humidifying system. All of these methods would produce humidity levels too high when used on a continuous basis resulting in a smaller percentage of chicks surviving the hatching process or poor post hatch performance.

The prior art includes U.S. Pat. No. 4,932,359 which discloses a process for sanitizing eggs by exposing the eggs to a solution of hydrogen peroxide during one or more stages of the hatchery process. The teachings of that patent are expressly limited to application until the actual time of pipping and hatching. Thus, there is no teaching of application after pipping. It is an object of the invention to have a method which will provide continuous protection for commercially raised poultry from the time the birds first break through the egg shell until they are removed from the hatchery environment.

It is still another object of the invention to provide such a method to decrease environmental microbial contamination without adversely affecting the proportion of birds that survive the hatching process.

It is another object of the invention to provide a method to accomplish the above which would not adversely affect the post hatch performance of the poultry.

SUMMARY OF THE INVENTION

It has now been found that these and other objects of the invention may be attained in a method in which a disinfectant solution is administered into the environment of newly hatched poultry after the point the birds break through the eggshell up until the time they are removed from the hatchery environment. The method permits a disinfectant solution to be administered continuously during this time period without adversely affecting the proportion of chicks that survive the hatching process or subsequent post hatch performance.

In one form of the invention a microaerosol dispensing apparatus is utilized to disperse the disinfectant solution. Ordinarily the microaerosol apparatus will provide a particle size in the range of 1 to 100 microns. The microaerosol dispensing apparatus may be of various constructions including but not limited to specialized pneumatic driven nozzles, thermal foggers, high velocity airstreams with a venturi nozzle or ultrasonic apparatus. Such apparatus is known that will deliver solutions in the particle range referred to above. This type of application allows for continuous application of disinfectant solutions over an extended time period without adversely affecting the portion of chicks that survive the hatching process or post hatch performance of poultry due to excessive levels of moisture in the environment.

In some forms of the invention the disinfectant administered is hydrogen peroxide or glutaraldehyde or any other disinfectant which is (1) an effective antimicrobial agent, (2) minimizes the degree of physical damage to the avian respiratory tissue, (3) improves upon or does not decrease the percentage of chicks that survive the hatching process, (4) does not result in poor post hatch performance, and (5) is safe for people to work in the presence of the material.

While the invention has particular advantages when used in the hatchery environment it will be understood that it also has application to other closed environments in which the chicks are placed after being hatched. For example, the chicks may be placed in a closed truck and the microaerosol application may be administered inside the truck while the chicks are being transported. The closed environment is particularly advantageous because human beings will not be exposed to the disinfectant and the chicks will be enveloped by the disinfectant. Thus the invention contemplates microaerosol application of a disinfectant to newly hatched chicks in the hatcher, in the truck transporting the chicks, both the hatcher and the truck or any other closed chamber in which the chicks are placed.

DESCRIPTION OF THE PREFERRED EMBODIMENTS

Fumigation is widely used in the poultry industry as a method of disinfecting surfaces and environments and is normally synonymous with formaldehyde fumigation in meaning, in this industry. A major use of this method of fumigation has commonly been during the final stage of incubation in a hatcher to reduce the microbial contamination in this environment. Fumigation by definition is to expose to fumes or volatile compounds. Typically this process depends upon vaporization by evaporation, or by a chemical reaction to generate a gas. With formaldehyde fumigation in the hatcher environment, formaldehyde gas is generated by evaporating a formalin solution or by a chemical reaction of mixing potassium permanganate with formalin. This gas then saturates the environment mixing with the humidity to form formalin on a microscopic level to produce the active disinfectant action of this process.

Formaldehyde has been the method of choice for this application due to its effectiveness and ease of use, however the adverse properties of this product are restricting its future use.

The following discussion including examples will demonstrate how the present invention is new and unique in that it utilizes microaerosol technology to disperse disinfecting solutions into the environment of hatching and newly hatched avian species, and will replace formaldehyde fumigation typically used in the poultry industry.

The term microaerosol is used to describe the particle size of a solution when entering the hatcher environment and in the present invention is particles in the range of one to one hundred microns in diameter. Any device which produces particles in this size range may be acceptable for the present invention. Particle sizes in this range may be generated by ultrasound using various ultrasonic humidifiers provided they are compatible with the solution to be used. Alternatively, the microaerosol may be generated utilizing specialized pneumatic driven nozzles such as those produced by Atomizing Systems, Inc. Thermal foggers or high velocity airstream with venturi nozzles may also be suitable to this application.

The present invention is typically used in an incubator designed for hatching poultry or avian species including chicken, duck, quail, turkey or other fowl.

The device to discharge the microaerosol may be located exterior to or in the interior of the physical hatcher unit, however the actual discharge of solution should occur in a location whereby maximum dispersal by the hatchers normal air flow will occur. Preferably this would be at the normal point of entry of air or humidity into the hatcher.

The preferred solution in the present invention is hydrogen peroxide in a concentration of 1 to 3 percent. Levels of hydrogen peroxide above 3% may cause undesirable damage to tissues of the avian respiratory system when used in the present application. Incorporation of a stabilizing agent such as acetic or phosphoric acid in a concentration of 0.05%, maybe included to stabilize the effectiveness of the hydrogen peroxide in waters which are found to be incompatible with the ability to maintain hydrogen peroxide in solution. The commercial source of the hydrogen peroxide does not appear to be critical therefore any commercially available source may be used. In some cases it may be more convenient to stock concentrated $H_2O_2$ such as a 50% solution may be more convenient than 3% solutions. The user can in this case dilute the concentrated solution prior to utilization, however, concentrated forms may be somewhat caustic or irritating to people.

The solution dispersed utilizing the present invention need not be limited to hydrogen peroxide as will be demonstrated in an example to follow. The limiting conditions for a disinfecting solution used for the present method should be only its safety of use, effectiveness as an antimicrobial agent, minimal destructive properties to the tissues of the avian species being hatched as well as minimal destructiveness to equipment in which it is used.

The time of implementation of the present method is preferably at the point when pipping or physical exit of the bird from the shell begins. The method is preferably employed continuously until a point in time just prior to removal of birds from the hatcher. Ordinarily it will be desirable to allow enough time for the particular hatcher used to remove any airborne disinfectant from the hatcher environment via the normal air exchange unit of the machine to eliminate possible irritation to some humans.

The volume of the solution applied in a given time span will depend upon the type of hatcher used and the degree of air exchange in the given machine. The limiting condition on volume of solution applied is a volume which will effectively produce the desired antimicrobial action while not interfering with the normal relative humidity levels that are critical to the portion of chicks that survive the hatching process and to the post hatch performance. The volume of solution should also be able to be applied on a continuous basis during the hatch period. Advantageously, the microaerosol will also be applied in closed trucks that transport the chicks.

In order to more fully demonstrate the attendant advantages arising from the present invention, the following examples are set forth. It is to be understood that the following is by way of example only and is not intended as an undue limitation on the otherwise broad scope of the invention.

EXAMPLE 1

Affect of Microaerosol Administration of Disinfectant During Hatch Upon Hatcher Performance In this example a hatcher (manufactured by Chick Master Incubator Co.) was equipped with microaerosol producing nozzles (manufactured by Atomizing Systems Inc.), and calibrated in a manner to deliver 1 liter per hour of a solution of hydrogen peroxide. The nozzles were physically located on the inside of the hatcher in a position within one half meter of the machine humidity nozzle.

Chicken eggs were transferred from setters on day 17 of incubation to the experimental hatchers in a randomized manner to eliminate variation due to pre hatcher incubation source. The application of microaerosol was started after physical exit from the eggs had begun, 48 hours from the expected pull time. Those skilled in the art will understand that "pull time" is the nominal time when the poultry is removed from the hatcher. This will ordinarily be the time after the chickens are dry. Control hatchers were set up in trial 1 to include one hatcher unit with normal formaldehyde fumigation by evaporation of 59 ml of formalin over 3 hours for a 30 hour time period starting 39 hours before the expected pull time of chickens from the hatchers. The second control hatcher received no treatment after the transfer was completed. Hatchery performance was measured by hatchability, bacteriological culturing of chicken down from the hatcher environment, histological examination of tracheal tissue of chickens at time of pull from the hatchers, physical appearance of the chickens at point of pull and weight loss between setter (eggs) and hatcher (chickens).

As can be seen in Table 1, both fumigation with formaldehyde and microaerosol fumigation with $H_2O_2$ significantly decrease the microbial contamination in the hatcher environment as measured by the down test method when compared to the untreated hatcher. Hatchability was not altered by method of treatment in the hatcher. The histological examination of tracheal tissue indicates that fumigation with hydrogen peroxide causes much less respiratory tissue damage than caused by the conventional formaldehyde fumigation method, however it does cause some tissue damage compared to the untreated chickens. The physical appearance of the chickens at hatch was altered by method of hatcher treatment in that chickens from formaldehyde fumigation had a dark yellow coloration compared to untreated controls, while those from the microaerosol treatment with $H_2O_2$ had distinctly white (bleached) feathers, compared to untreated controls. All treatments produced chickens that other than color appeared active without any visible signs of respiratory distress. No difference was found between treatments in the amount of weight loss between eggs in setters and chickens out of hatchers, indicating that the microaerosol administration of disinfectant solution did not adversely alter the humidity level in the hatcher causing chickens to retain too much moisture.

EXAMPLE 2

Affect of Microaerosol Administration of Disinfectant During Hatch Upon Post Hatch Performance Experimental trials were carried out to examine the post hatch performance of chickens hatched with the various hatcher treatments alluded to in example 1 (trial 1), above. Sixteen experimental pens of chickens from each of the 3 hatcher treatments were set up with 128 birds per pen. The chickens were raised utilizing normal broiler growing methods in the same facility. Performance was measured in terms of growing mortality, live weight and feed conversion (in terms of pounds of feed to pounds of live chicken produced). The experiment was concluded when the chickens reached 53 days of age. The experimental data is tabulated in Table 2. There appears to have been little difference in terms of live weight and feed conversion due to the various hatcher treatments, however the microaerosol administration of disinfectant ($H_2O_2$), appears to have beneficial affects upon decreasing growing broiler chicken mortality. This decreased mortality rate was possibly due to the decreased microbial contamination in the hatcher compared to chickens from the untreated hatcher, or due to the lower degree of damage to the respiratory system than observed in chickens treated in the hatcher with formaldehyde fumigation.

EXAMPLE 3

Affect of Microaerosol Administration of Disinfectant During Hatch Upon Hatchery Performance This example is similar to Example 1 except that the disinfectant solution used was one percent glutaraldehyde in place of hydrogen peroxide. In this example hatchers manufactured by Chick Master Incubator Co. were equipped with microaerosol producing nozzles made by Atomizing Systems Inc., and calibrated in a manner to deliver two thirds of a liter per hour of a one percent solution of glutaraldehyde. The nozzles were physically located on the inside of the hatcher in a position within one half meter of the machine humidity nozzle.

Chicken eggs were transferred from setters on day 17 of incubation to the experimental hatchers. The application of microaerosol was started after physical exit from the eggs had begun, 36 hours from the expected pull time. Control hatchers were set up to include two hatcher units with normal formaldehyde fumigation by evaporation of 59 ml of formalin every 3 hours for a 30 hour time period starting 39 hours before the expected pull time of chickens from the hatchers. The second control hatcher received no treatment after the transfer was completed. Hatchery performance was measured by the portion of chicks surviving the hatching process, bacteriological culturing of chickens taken from the hatcher environment, and physical appearance of the chickens at point of pull.

As can be seen in Table 3, both fumigation with formaldehyde and microaerosol fumigation with glutaraldehyde significantly decrease the microbial contamination in the hatcher environment as measured by the down test method when compared to the untreated hatcher. Hatchability was not decreased by the glutaraldehyde fumigation in the hatcher. The physical appearance of the chickens at hatch was not altered by method of hatcher treatment except that the formaldehyde fumigated chickens were more yellow in appearance than the other two groups. All treatments produced chickens that other than color appeared active without any visible signs of respiratory distress.

EXAMPLE 4

Affect of Microaerosol Administration of Disinfectant During Hatch Upon Hatchery Performance This example describes a variation of the present method whereby the microaerosol was generated via a Holmes Air ultrasonic humidifier which was placed inside a Chickmaster hatcher at the point chickens were starting to break out of the respective shells. A solution of 2.5% hydrogen peroxide was applied via the ultrasonic humidifier on a continuous basis for a 36 hour time period with an application rate of 0.55 liters per hour.

Chicken eggs were transferred from setters on day 17 of incubation and transferred in a randomized manner to the experimental hatchers. A control hatcher was set up which received no treatment after the transfer was completed. Hatchery performance was measured by hatchability, bacteriological culturing of chicken down from the hatcher environment, and physical appearance of the chickens at point of pull.

As can be seen in Table 4 microaerosol fumigation with hydrogen peroxide applied via the ultrasonic humidifier significantly decreased the microbial contamination in the hatcher environment as measured by the down test method when compared to the untreated hatcher. Hatchability in this example was improved by the application of disinfectant into the hatcher environment. The physical appearance of the chickens at hatch was altered by method of hatcher treatment in that the hydrogen peroxide treated chickens had bleached (white) feathers following treatment when compared to the untreated controls. No signs of respiratory distress were observed in either group.

TABLE 1

HATCHERY PERFORMANCE DATA FROM VARIOUS HATCHER TREATMENTS

| Hatcher Treatment | Number Eggs in Hatcher | Hatch % | Hatcher Chick Down Micro-organisms per gram | Histological Examination of Tracheal tissue |
|---|---|---|---|---|
| None | 9558 | 65.8 | >30,000 | Cilia intact, no glandular cell hyperplasia |
| Fumigation Formaldehyde | 9373 | 66.6 | 400 | Extensive cilia loss, epithelial disruption and capillary distention with edema |
| Microaersol Fumigation 2.5% $H_2O_2$ | 9558 | 65.7 | <100 | Some cilia loss, distinct glandular cell hyperplasia |

TABLE 2

POST HATCH PERFORMANCE DATA FROM VARIOUS HATCHER TREATMENTS OF 53 DAY OLD CHICKENS

| Hatcher Treatment | Number of chickens placed | Mortality Percent | Live Body Weight (Pounds) | Feed Conversion |
|---|---|---|---|---|
| None | 1984 | 6.96 | 5.288 | 2.248 |
| Fumigated Formaldehyde | 1984 | 6.70 | 5.280 | 2.237 |
| Microaersol Fumigation 2.5% $H_2O_2$ | 1984 | 5.24 | 5.280 | 2.231 |

TABLE 3

HATCHERY PERFORMANCE DATA FROM VARIOUS HATCHER TREATMENTS

| Hatcher Treatment | Number of Eggs in Hatcher | Hatch Percent of eggs | Hatcher Chick Down Microorganisms per gram |
|---|---|---|---|
| Glutaraldehyde | 9720 | 79.2 | 1,000 |
| None | 9720 | 74.4 | >30,000 |
| Formaldehyde | 9720 | 73.6 | <100 |
| Formaldehyde | 9720 | 72.5 | <100 |

TABLE 4

HATCHERY PERFORMANCE DATA FROM VARIOUS HATCHER TREATMENTS

| Hatcher Treatment | Number Fertile Eggs in Hatcher | Hatch of Fertile Eggs % | Hatcher Chick Down Microorganisms per gram |
|---|---|---|---|
| None | 5939 | 74.3 | >30,000 |
| Ultrasonic Microaersol Fumigation 2.5% $H_2O_2$ | 5862 | 78.4 | 400 |

The method in accordance with the invention provides a safe effective means of reducing microbial contamination from the environment after the poultry begin to hatch from the egg. In addition the method in accordance with the invention allows for the safe administration of disinfectant solutions with minimal exposure of people to the disinfectant. The application is capable of being automated to eliminate handling of potentially hazardous materials by hatchery personnel.

It will be seen from the examples and descriptions above that the invention attains the following objectives.

(a) Providing a reliable, efficient, and safe method for administering disinfectant solutions into the environment of hatching poultry after the point when actual exit from the egg begins, for the purpose of decreasing the level of microbial organisms in this environment.

(b) Providing a method to allow continuous administration of disinfectant solutions into the environment of hatching poultry in a manner which does not introduce levels of moisture into this environment which would interfere with normal hatchability or post hatch performance.

(c) Providing a method to administer disinfectant solutions which will minimize the damaging affects of the solutions upon the tissues of the avian respiratory system whereby post hatch performance will not be decreased and may be improved by said treatment.

Other variations of the present invention will be apparent to those skilled in the art upon exposure to the teachings herein. For example, those skilled in the art will recognize, for example, there may be variations in the location of the source of microaerosol producing device, the type of device used to produce the desired particle range of solution to be administered, and the solutions used in the method will occur without changing the desired scope of the invention. Such other variations are deemed to be encompassed by the disclosure, the invention being delimited only by the following claims.

Having thus described our invention we claim:

1. A method of reducing microorganism contamination of the environment of newly hatched poultry which comprises:
   providing a microaerosol apparatus for producing a microaerosol spray;
   providing a disinfectant;
   dispensing the disinfectant with the microaerosol apparatus in a substantially closed chamber in which newly hatched poultry are disposed substantially continuously from the time of initial pipping until essentially all the poultry have exited from their respective eggs.

2. A method according to claim 1 further including:
   continuing the dispensing step until the newly hatched poultry is removed from the closed chamber.

3. A method as described in claim 1 wherein:

said providing apparatus step includes providing apparatus which will deliver the disinfectant at a particle size of between one to one hundred microns in diameter.

4. A method as described in claim 2 wherein:

said providing apparatus step includes providing apparatus which will deliver the disinfectant at a particle size of between one to one hundred microns in diameter.

5. A method according to claim 4 wherein:

the step of providing the apparatus for producing a microaerosol spray includes providing apparatus that utilizes ultrasound.

6. A method according to claim 4 wherein:

the step of providing the apparatus for producing a microaerosol spray includes providing apparatus that utilizes air having a pressure greater than ambient air pressure.

7. A method according to claim 4 wherein:

the step of providing apparatus for producing a microaerosol spray includes providing apparatus that utilizes a moving stream of air.

8. A method of reducing microorganism contamination of the environment of newly hatched poultry which comprises:

providing apparatus for producing a microaerosol spray;

providing a disinfectant;

dispensing the disinfectant with the microaerosol apparatus in a substantially closed chamber in which the newly hatched poultry are disposed for a plurality of hours.

9. The method as described in claim 8 wherein:

said plurality of hours is substantially 36 hours.

10. The method as described in claim 8 wherein:

said plurality of hours is substantially 48 hours.

11. A method as described in claim 8 wherein:

said providing step includes providing apparatus which will deliver the disinfectant at a particle size of between one to one hundred microns in diameter.

12. A method as described in claim 9 wherein:

said providing step includes providing apparatus which will deliver the disinfectant at a particle size of between one to one hundred microns in diameter.

13. A method according to claim 10 wherein:

the step of providing the apparatus for producing a microaerosol spray includes providing apparatus that utilizes ultrasound.

14. A method according to claim 11 wherein:

the step of providing apparatus for producing a microaerosol spray includes providing apparatus that utilizes a stream of air.

15. A method according to claim 12 wherein:

the step of providing apparatus for producing a microaerosol spray includes providing apparatus that utilizes thermal energy.

16. A method according to claim 13 wherein:

the disinfectant comprises hydrogen peroxide.

17. A method according to claim 14 wherein:

the disinfectant comprises hydrogen peroxide.

18. A method according to claim 17 wherein:

the disinfectant comprises hydrogen peroxide.

19. A method of reducing microorganism contamination of the environment of newly hatched poultry which comprises:

providing a microaerosol apparatus for producing a microaerosol spray;

providing a disinfectant;

dispensing the disinfectant with the microaerosol apparatus in a substantially closed chamber in which newly hatched poultry are disposed for a plurality of hours without affecting the portion of chicks that survive the hatching process or post hatch performance of poultry due to excessive levels of moisture.

* * * * *